US008309063B2

United States Patent
SenGupta et al.

(10) Patent No.: US 8,309,063 B2
(45) Date of Patent: Nov. 13, 2012

(54) STABLE SUNSCREEN COMPOSITIONS CONTAINING ZINC OXIDE

(75) Inventors: Ashoke K. SenGupta, Barrington, IL (US); Ilona Lin, Wauconda, IL (US)

(73) Assignee: Amcol International Corporation, Hoffman Estates, IL (US)

( * ) Notice: Subject to any disclaimer, the term of this patent is extended or adjusted under 35 U.S.C. 154(b) by 1427 days.

(21) Appl. No.: 11/150,053

(22) Filed: Jun. 10, 2005

(65) Prior Publication Data

US 2006/0280702 A1  Dec. 14, 2006

(51) Int. Cl.
- A61K 8/00 (2006.01)
- A61K 8/18 (2006.01)
- A61K 9/00 (2006.01)
- A61K 8/02 (2006.01)
- A61K 33/00 (2006.01)
- A61K 33/40 (2006.01)
- A61Q 17/04 (2006.01)
- A01N 59/00 (2006.01)
- A01N 39/00 (2006.01)

(52) U.S. Cl. ............ 424/56; 424/59; 424/400; 424/401; 424/600; 424/614

(58) Field of Classification Search .................. 424/56, 424/59, 400, 401, 600, 614
See application file for complete search history.

(56) References Cited

U.S. PATENT DOCUMENTS

| 4,323,694 | A | * | 4/1982 | Scala, Jr. .................... 560/103 |
| 6,500,411 | B2 | | 12/2002 | SenGupta et al. |
| 2002/0182155 | A1 | | 12/2002 | SenGupta et al. |

FOREIGN PATENT DOCUMENTS

| EP | 0559319 | 9/1993 |
| EP | 0619999 | 10/1994 |

OTHER PUBLICATIONS

International Search Report for PCT/US2006/007233.

* cited by examiner

*Primary Examiner* — Mina Haghighatian
*Assistant Examiner* — Luke Karpinski
(74) *Attorney, Agent, or Firm* — Marshall, Gerstein & Borun LLP

(57) ABSTRACT

A stable, oil-in-water (O-W) emulsion-based sunscreen composition having at least one water-insoluble, organic UV-absorber having a water-solubility of much less than 0.1% by weight, contained in the oil phase of the sunscreen emulsion, comprising i) zinc oxide (ZnO) particles having a surface free of any prior coating of any inorganic oxide and hydrophobic material, remaining dispersed in the water phase of the sunscreen emulsion; ii) at least one non- or low-foaming, non-cationic, hydrophilic polymer, capable of dispersing or deflocculating the ZnO particles but incapable of thickening an aqueous composition to a viscosity of greater than 100 cps at 25° C., wherein the viscosity is measured using a Brookfield viscometer operated at 10 rpm for 15 seconds, when the polymer is added at an amount of 1%, based on the total weight of the polymer and water in the aqueous composition; iii) at least one phenolic polymer, capable of functioning as a dispersing or deflocculating agent for particulate material(s), and adsorbing at an oil-water interface; and v) a buffering agent for the water phase of the sunscreen emulsion.

25 Claims, No Drawings

STABLE SUNSCREEN COMPOSITIONS CONTAINING ZINC OXIDE

FIELD OF THE INVENTION

An amphoteric metal oxide, capable of absorbing UVA radiation, zinc oxide (ZnO) is among the few UVA sunscreens approved for use in sun protection products. Despite its relatively low cost, and the limited selection of UVA sunscreens, its rampant use in sunscreen products has not been realized to date. This is mainly because considerable difficulties are met in stabilizing sunscreen compositions if they contain pristine ZnO. The problems arise due to certain properties that this hydrophilic, particulate material exhibits in aqueous suspensions. The solutions claimed in the prior art forgo the cost effectiveness of pristine ZnO, yet fail to offer sound reliability, having to rely on coating the ZnO particles with hydrophobic materials. Such hydrophobically-modified ZnO is invariably far more expensive than pristine ZnO. Also, perfecting surface-coverage of every primary particle contained in a given weight of ZnO solids is practically impossible.

The present invention addresses this void, disclosing novel methods of circumventing the instability-problems typically encountered with ZnO, in turn providing compositions for stable, oil-in-water (O-W) sunscreen emulsions that contain pristine ZnO. In these emulsions, the ZnO particles remain dispersed in the water phase of the emulsions, preferably in a highly deflocculated form. The use of pristine ZnO minimizes the cost, while the deflocculated ZnO particles present a greater surface area for the attenuation of UV rays than otherwise. As a further benefit, these sunscreen emulsions show sun protection factors (SPF) that are significantly higher than what might be generally obtained from a given combination of UV absorbers in O-W sunscreen emulsions.

BACKGROUND OF THE INVENTION

It is well recognized that the solar ultraviolet (UV) radiation poses serious threat of human skin damage which may range from the short term hazard like erythema, i.e., sunburn to long term hazards like skin cancer and/or premature aging of the skin. The UV radiation having a wavelength of from 290 nm to 320 nm, generally referred to as the UVB radiation, is what is known to cause erythema. On the other hand, numerous reported studies point to unprotected skin exposure to the UV radiation having a wavelength of from 320 nm to 400 nm as being the primary cause of skin cancer. It is essential, therefore, that the skin is protected from both UVA and UVB radiations in order to avoid long and short term deleterious effects of solar radiation.

The SPF (Sun Protection Factor) rating system has been developed to help consumers select the appropriate sun protection product for any given outdoor activity involving exposure to the sun. The SPF number corresponds to the multiplying factor by which the duration of protection by a properly applied sunscreen exceeds the exposure time that causes the unprotected skin to show darkening. Thus, with proper application of an SPF 15 product, a person should be able to remain in the sun without skin darkening for fifteen times the usual unprotected duration.

In recent years, due to the increased public awareness of the aforementioned hazards of UV radiation, the use of sun protection products has grown considerably, with consumers preferring products that offer protection over the entire range of UV radiation, i.e., from 290 nm to 400 nm. Nonetheless, while there are several UVB absorbing materials approved for use in sun protection products by the regulatory agencies in different countries, the number of approved UVA absorbers is far less. Among these approved UVA sunscreens is the amphoteric metal oxide, zinc oxide (ZnO).

Most personal care and cosmetic products in the form of lotions and creams are essentially either oil-in-water (O-W) or water-in-oil (W-O) emulsions, with the majority being O-W emulsions. Most of these O-W emulsion-based compositions contain various additives including emulsifiers and thickening agents, many of which bear negatively-charged, i.e., anionic functional groups. Adding positively-charged, i.e., cationic ingredients such as cationic surfactants, polymers, and particulate solids at a relatively high dosage to emulsions that contain anionic emulsifiers and thickeners poses a high risk of destabilizing the emulsions. The electrostatic attraction between oppositely charged moieties mixed in a formulation may render these ingredients functionally ineffective and/or insoluble, which in turn is bound to produce unstable emulsions.

Such instability generally manifests in various forms including separation of the oil phase and/or the water phase of the emulsion, precipitation of otherwise soluble materials, separation of solid particulate materials otherwise meant to remain suspended in the emulsion, undesirable thinning of the emulsion, excessive thickening of the emulsion, and pH-shift. Some of these instability problems may arise also if the water phase of an O-W emulsion contains relatively high amounts of dissolved cations, especially the multivalent cations, along with substantial quantities of anionic and/or electrolyte-sensitive additives.

Zinc oxide, available in the form of a finely milled particulate material, exhibits properties that present considerable challenge in producing stable O-W emulsions that were to contain anionic and/or electrolyte-sensitive additives. Over a wide range of pH, ZnO particles tend to have a cationic surface charge, when suspended in water or an electrolyte solution. Also, the pH of minimum solubility for zinc cations is considerably high, in the range of 9.5-10.5, implying that increased dissolution of zinc cations from zinc oxide solids may occur between the pH of 6 and 9, the typical pH range for most personal care products. Adding further complexity, solubilization of zinc cations from zinc oxide may be enhanced in the presence of certain anionic surfactants having weak acid groups such as phosphate, carboxylate, phenolate, and phosphonate groups, which are often used as anionic emulsifiers for O-W emulsions.

Unless countermanded, the aforementioned detrimental properties of ZnO would cast a stronger influence if the ZnO particles are dispersed in the water phase of O-W emulsions. In other words, the adverse effects of ZnO on emulsion stability could be minimized if the ZnO particles are contained in the oil phase of the emulsion and thus precluded from entering the water phase of the emulsion, as taught in the U.S. Pat. No. 6,464,965 B1. However, since the surface of these particles is hydrophilic, dispersing them in the oil phase would require hydrophobic modification of the surface via covalent-bonding of hydrophobic materials (e.g., silane), and/or by using wetting agents or dispersing agents. These approaches, however, would add considerable cost, yet might fail to provide sound reliability, and could lead to various other formulation problems, for reasons such as the following:

i) During bulk manufacturing using ordinary solid-liquid mixing processes, it would be impossible to ensure complete surface-coverage of all primary (single) ZnO particles contained in a given weight of ZnO solids, via covalent-bonding of hydrophobic surface modifying agents.

ii) Such coated ZnO would be considerably more expensive than pristine ZnO.

iii) The more-effective wetting or dispersing agents that might be used for dispersing pristine ZnO particles in hydrophobic or oily liquids would be the surfactants and/or the polymers that also find use as emulsifiers for water-in-oil (W-O) emulsions. The presence of excess amounts (corresponding to relatively high dosage levels of ZnO) of these W-O emulsifiers in O-W sunscreen emulsions may lead to difficulties in stabilizing the emulsions, especially if the emulsions' oil phase content is relatively high, as might be in high-SPF sunscreen products. Increasing the dosage of the O-W emulsifiers might help in counteracting the effects of the W-O emulsifiers, but the concomitant increase in detergency due to the O-W emulsifiers is likely to present problems in achieving good water-repellency for the sunscreen, a highly desirable feature for most sun protection products.

Yet another way of avoiding the instability problems induced by ZnO would be to coat the ZnO particles with other hydrophilic, inorganic oxide materials, e.g., titanium dioxide and silicon dioxide, which, unlike ZnO, are not likely to hamper the stability of O-W emulsions. These coated ZnO materials, however, would be considerably more expensive than pristine ZnO.

The U.S. Pat. No. 6,500,411 B2 discloses the use of particulate materials including ZnO for boosting the SPF of emulsion-based sunscreen compositions, requiring that the particulate materials remain dispersed in the water phase of the emulsions, and that certain phenolic polymers render the particles capable of resisting agglomeration or flocculation in these compositions. The invention demonstrates that aqueous dispersions comprised of particulate materials such as titanium dioxide (TiO2), particulate-based thickeners such as smectite clays, and certain water-soluble phenolic polymers such as lignosulfonate used as a dispersing agent for the suspended solids, when added to sunscreen emulsions containing at least one organic UV absorber, increase the SPF largely. In contrast, similar aqueous dispersions of the aforementioned particulate solids, but without any lignosulfonate contained therein, produce no SPF boost. Also, substituting sodium polyacrylate for lignosulfonate as the dispersing agent greatly reduces the SPF boost. The invention, however, does not specify nor address any issues concerning the stability of the sunscreen compositions disclosed therein.

Nonetheless, it was found during the course of the research leading to the present invention that ZnO-containing sunscreen compositions of the type described in the aforementioned patent exhibited an extraordinary behavior in terms of stability inasmuch as their stability seemed to depend on the manufacturing process, although in a counterintuitive sense. An O-W sunscreen emulsion that contained in its water phase 2% by weight of ZnO exhibited poor stability, when produced using a high-shear homogenizer. On the other hand, the same emulsion could be manufactured in a more stable form when an agitator was used instead during emulsion-making. Typically, a high-shear homogenizer is more effective than an agitator in producing stable emulsions. Also, the instability manifested as the separation of the water phase as localized or spotty water pools, appearing mostly at the surface of the emulsion, rather than of the oil phase of the emulsions, whereas an unstable O-W emulsion would typically show the reverse.

It is speculated that this peculiar stability behavior of the foregoing emulsion is due to phenomena such as the following: Air is entrapped within the emulsion during its manufacturing, which takes on the form of ultra-fine air bubbles in the presence of a moderately foaming polymer such as lignosulfonate and under the action of a high-shear homogenizer. Under the destabilizing influence of ZnO, these ultra-fine air bubbles undergo coalescence ultimately, thus growing bigger in size. Eventually, the collapsing of numerous air bubbles upon reaching the surface of the emulsion sample produces the spotty liquid pools at the emulsion surface.

Even though the technology disclosed in the U.S. Pat. No. 6,500,411 B2 is currently being used widely for producing commercial sunscreen products that do not contain ZnO, its use in producing ZnO-laden sunscreen products may have limited commercial viability because of the instability issues described above.

An object of the present invention, therefore, is to provide ZnO-containing O-W sunscreen emulsion compositions which exhibit a high level of physicochemical stability, yet not requiring i) the ZnO particles to be coated with either any other water-insoluble inorganic material or water-insoluble organic material; and ii) the ZnO particles to be contained substantially in the oil phase of the emulsions. A related object is to obtain ZnO-laden, yet, highly stable O-W sunscreen emulsion compositions wherein the ZnO particles remain dispersed in the water phase of the emulsions, preferably in a highly deflocculated form.

Most commercial sunscreen products utilize high levels of organic UV absorbers which tend to be expensive and are oil-like and/or oil-soluble materials, in achieving high SPF values. These high levels of sunscreen actives increase the cost of the product, while rendering the product less appealing for its greasy skin feel and skin irritation. A further object of the present invention, therefore, is to provide O-W sunscreen emulsion compositions having pristine ZnO particles dispersed in the water phase, which exhibit higher SPF values as compared to conventional O-W sunscreen emulsions, for a given loading of organic UV absorbers contained therein.

SUMMARY OF THE INVENTION

The present invention discloses stable sunscreen compositions for the broad spectrum (i.e., covering both UVA and UVB ranges of wavelength) protection of the human skin from solar radiation. These sunscreen compositions, produced preferably in the form of oil-in-water (O-W) emulsions, contain pristine zinc oxide (ZnO) as a UVA absorber, preferably in combination with at least one UVB absorber, and are inherently capable of providing for high SPF boosts. According to a preferred embodiment, the ZnO particles remain dispersed in the water phase (continuous phase) of the O-W emulsions, preferably in the form of highly deflocculated particles. Certain hydrophilic polymers that do not exhibit foaming and/or emulsifying properties are used as a dispersing agent to effect deflocculation of the ZnO particles. These sunscreen emulsions may further contain at least one other inorganic and/or organic particulate material besides ZnO. Preferably, the non-ZnO particulate material remains dispersed as highly deflocculated particles in the water phase of the emulsions, under the surface-modifying influence of one or more dispersing agent selected from certain water-soluble, phenolic polymers that can also act as an emulsifying agent for O-W emulsions. Any organic UV absorber contained in these emulsions, remains dissolved in the oil phase of the emulsions. The emulsions may further contain emulsifiers, emollients, fatty alcohols and esters, water-phase thickening agents, oil-phase thickening agents, organic hydrophilic liquids such as glycols and glycerin, chelating agents, waterproofing agents, film-forming agents, buffering agents, moisturizing agents, sensory property boosting agents, antioxidants, vitamins, and preservatives.

DETAILED DESCRIPTION OF THE INVENTION

The present invention relates to stable, oil-in-water (O-W) emulsion-based sunscreen compositions that contain pristine ZnO in the water phase of the emulsions, and are inherently capable of providing for high SPF boosts. According to the most preferred embodiment of the present invention, these sunscreen emulsions meet all of the following compositional requirements.

i) The pristine ZnO particles remain dispersed as highly deflocculated particles in the water phase of the emulsion, under the surface-modifying influence of one or more hydrophilic polymer acting as a dispersing/deflocculating agent for the particles, with the polymer(s) being necessarily such that they do not exhibit foaming and/or emulsifying properties. The mean primary particle size for the ZnO particles is preferably <3 micron, more preferably less than 1 micron, and most preferably less than 0.5 micron. The preferred hydrophilic polymers include, but not limited to, homopolymers and copolymers of polycarboxylate, polysulfonate, polyphosphate, polyphosphonate, polyethylene glycol, and polyvinyl alcohol, having a weight-averaged molecular weight, Mw, in the range of 1,000-500,000 Dalton. The most preferred polymer for the object of the present invention is sodium polyacrylate having a weight-averaged molecular weight, Mw, in the range of 5,000-50,000 Dalton. The amount of pristine ZnO contained in the sunscreen emulsions can be in the range of 2-25%, based on the weight of the emulsions. The amount of the hydrophilic polymer(s) contained in the sunscreen emulsions is from about 0.1% to about 100%, more preferably from about 1% to about 50%, and most preferably from about 10% to about 30%, based on the weight of pristine ZnO.

ii) The water phase of the emulsion further contains one or more phenolic polymer selected from the group consisting of lignosulfonate, lignin, oxylignin, humate, and any of their derivatives including their copolymers. These polymers are necessarily such that they can function not only as a dispersing agent for various inorganic and organic particulate materials, but also as an emulsifying agent by virtue of being able to adsorb at an oil-water interface.

iii) The amount of the phenolic polymer contained in the sunscreen emulsions is preferably in the range of 0.01-1%, more preferably in the range of 0.05-0.5%, and most preferably in the range of 0.1-0.3%, based on the weight of the emulsions.

iv) The polymer(s) used as the dispersing agent for ZnO are compatible with the foregoing phenolic polymer(s), i.e., there is no phase-separation or precipitation of any of the polymers upon mixing in an aqueous solution.

v) The water phase of the sunscreen emulsions preferably contains buffering agent(s) at a level of from 0.05 to 3% by weight of the sunscreen emulsions.

vi) Other than the aforementioned phenolic polymer(s), any emulsifier(s) used in producing the sunscreen emulsions preferably do not contain any metal-chelating functional groups, non-limiting examples of which include phosphate, carboxylate, phenolate, and phosphonate groups. The emulsifiers suitable for the object of the present invention include, but not limited to alkyl sulfates, alkyl ether sulfates, alkaryl sulfonates, α-olefin sulfonates, polyalkyl glucosides, ethoxylated alkyl esters, and glyceryl esters. The alkyl groups generally contain from 8 to 18 carbon atoms and may be unsaturated. The level of the emulsifier(s) may range preferably from 0.05 to 30%, more preferably from 0.1 to 20%, and most preferably from 0.5 to 10% by weight of the sunscreen emulsions.

vii) The pH of the emulsion is preferably in the range of 7.5-10, more preferably in the range of 8-9.5, and most preferably in the range of 8.5-9.

Failing to meet all of the above compositional requirements may result in not achieving the full benefit of the present invention, including overcoming the limitations of prior art compositions. For example, it was found during the course of the present invention that, fulfilling the compositional requirements (i) through (v) did not produce stable sunscreen emulsions, unless the compositional requirements (vi) and (vii) were also fulfilled.

Also, as apparent from the comparative examples presented in the U.S. Pat. No. 6,500,411 B2, sunscreen emulsions having particulate materials dispersed in the water phase of the emulsions, would exhibit a much lower SPF boost if sodium polyacrylate, rather than lignosulfonate, was used as the dispersing agent for the particulate materials. Stated differently, unless the sunscreen compositions included one or more of the aforementioned phenolic polymers as a dispersing agent for the particulate materials contained therein, there might not be as much of an SPF boost.

On the other hand, the presence of these phenolic polymers at relatively high levels in ZnO-laden sunscreen emulsions, (as might be the case when these polymers are used solely in deflocculating relatively large amounts of the particulate materials), could cause excessive air entrapment which in turn might lead to various instability issues. In other words, if the sunscreen emulsions were to contain a minimum of 2% by weight of ZnO as a UVA absorber, a low-foaming, hydrophilic polymer, for example, sodium polyacrylate, would have to be used as the dispersing agent for ZnO, in order to achieve emulsion stability.

In the preceding sections, the term "pristine ZnO" refers to particulate solids of ZnO, wherein the particle surface is not coated with any inorganic and/or organic material prior to its use in the sunscreen compositions of the present invention. The term "dispersing agent" refers to an additive that can effectively minimize agglomeration or flocculation of particulate materials suspended in a liquid. This generally requires that the additive adsorbs onto the surface of suspended particles, and provides for electrostatic and/or steric repulsions between the particles, as described in colloid literature. For most particulate materials, a way to evaluate the effectiveness of an additive as a dispersing agent is to measure the viscosity of their concentrated (>25% by weight) suspensions with and without the additive. The additive is considered to be an effective dispersing agent if the suspension viscosity is reduced significantly upon the addition of the additive. The term "emulsifying agent" refers to an additive that can effectively emulsify one liquid (e.g., oil) in a second liquid (e.g., water) that is immiscible with the first liquid, producing an emulsion of liquid 1 in liquid 2, that remains stable against separation of any of the two liquid phases from the emulsion over long durations. The term "SPF boost" relates to the situation wherein, upon addition of an additive to a sunscreen composition, the SPF value of the sunscreen increases significantly from the value typically obtained for the sunscreen, for a given combination of UV absorbers contained therein—albeit the additive, at the dosage used, hardly has any significant contribution towards UV-absorbance, due to itself.

The sunscreen emulsions of the present invention may further contain one or more particulate material (water-insoluble) other than ZnO, in the form of submicron-sized particles, with a mean primary particle size of preferably less than 5 microns, more preferably less than 0.5 micron, and most preferably less than 0.1 micron, wherein the particles remain deflocculated under the surface-modifying influence of one or more of the aforementioned phenolic polymers acting as a dispersing agent for the particulate materials. The preferred particulate materials include, but not limited to inorganic oxides, silicate minerals, and water-insoluble inorganic salts, non-limiting examples of which include titanium dioxide, fumed alumina, fumed silica, alumina, silica, aluminum trihydrate, bentonite, kaolinite, talc, cerium oxide, calcium carbonate, calcium sulfate, and various latex polymers. The amount of these particulate materials contained in the sunscreen emulsions can be in the range of 0.05-3%, but more preferably in the range of 0.1-2%, and most preferably in the range 0.5-1%, based on the weight of the emulsions.

The sunscreen emulsions of the present invention may also contain one or more water-phase thickening agents including smectite clays and high molecular weight and/or cross-linked polymers. The polymeric thickening agents are preferably not hydrophobically-modified. Non-limiting examples of the preferred polymeric thickening agents include cross-linked polyacrylate (Carbopol 980 from B. F. Goodrich Company), xanthan gum, polysaccharide (cellulose polymers from Amerchol Corporation), polyethylene glycol, and polyacrylamide. Among the preferred polymeric thickening agents, the most preferred polymers are those that either are free of any metal-chelating functional groups such as carboxylate, phosphate, phenolate, and phosphonate groups, or contain only small amounts of these functional groups. The water-phase thickening agent may be included in the sunscreen compositions of the present invention in an amount of from 0.01 to 5%, and more preferably in an amount of from 0.05 to 2%, and most preferably in an amount of from 0.1 to 1% by weight of the compositions.

The sunscreen emulsions of the present invention may further contain emollients, fatty alcohols and esters, oil-phase thickening agents such as oragnoclays, waxes, and polymeric thickeners, hydrophilic liquids such as glycols and glycerin, chelating agents, waterproofing agents, film-forming agents, moisturizing agents, sensory property boosting agents, antioxidants, vitamins, preservatives, fragrances, and coloring pigments and dyes.

The following examples will more fully illustrate the preferred embodiments within the scope of the present invention. These examples are solely for the purpose of illustration and are not to be construed as limitations of the present invention as many variations thereof are possible without departing from the purview and spirit of the invention.

EXAMPLE I

This example shows the compositions (Table I) and the method of manufacturing of aqueous dispersions of mixtures of pristine ZnO, titanium dioxide (TiO2), and smectite clay, which are subsequently incorporated into sunscreen emulsion formulations in order to produce the sunscreen compositions of the present invention.

TABLE I

| Ingredient | Phase | Dispersion # 1 Batch Size: 849 gm, % by weight | Dispersion # 2 Batch Size: 1041.27 gm, % by Weight |
|---|---|---|---|
| Deionized Water | A | 70.67 | 57.62 |
| Borax, $10H_2O$ | A | 1.18 | 0.96 |
| Sodium Polyacrylate (Sokalan PA 30CL, 45% active, from BASF Corporation) | A | 3.30 | 6.72 |
| Zinc Oxide—ZnO | B | 11.78 | 24.01 |
| Smectite Clay (AMCOL International) | C | 5.89 | 4.80 |
| Lignosulfonate (Ultrazine NAC, 92% active, from Borregaard) | D | 1.36 | 1.11 |
| Titanium Dioxide—$TiO_2$ | E | 4.42 | 3.60 |
| 50% Sodium Hydroxide | F | 0.14 | 0.12 |
| Preservative | F | 1.13 | 0.96 |
| Antifoaming Agent | G | 0.13 | 0.10 |

Manufacturing Procedure

In a suitable vessel, combine the Phase A ingredients in the order shown in Table I.

Mix thoroughly in a rotor-stator homogenizer (Silverson homogenizer) until the borax solids dissolve completely.

Add Phase B in small portions, while the batch is being homogenized at 4,000 rpm. While maintaining the temperature below 30° C., continue mixing/homogenizing for at least 15 minutes, once all of the ZnO has been added to the batch.

Add Phase C in small portions, while homogenizing the batch at 5,000-7,500 rpm, maintaining the temperature below 30° C.

Continue homogenizing the batch until it looks uniform or lump-free.

Add Phase D in small portions, while the batch remains under mixing and its temperature maintained below 30° C.

Once Phase D dissolves completely, start adding Phase E in small portions, while continuing to homogenize the batch.

Once all the TiO2 has been added, increase the homogenizer speed to 8,000 rpm, and continue homogenizing the batch for at least 10 minutes.

Add the Phase F ingredients in the order shown in the recipe (Table I) and mix well.

After reducing the homogenizer speed to 3,000 rpm, add Phase G. Continue mixing for an additional 30 minutes, while maintaining the temperature below 30° C.

It may be noted that non-limiting examples of personal care and cosmetic products wherein the foregoing aqueous dispersions of zinc oxide may be used include any emulsion-based products that were to contain zinc oxide in the emulsions' water phase, including water-in-oil emulsion and water-in-silicone emulsions.

EXAMPLE II

This example shows the compositions and the method of manufacturing of stable sunscreen emulsions of the present invention. These sunscreen emulsions contain about 2% by weight of ZnO. They further contain smectite clay and xanthan gum as the water-phase thickening agents, and an anionic emulsifier, sodium cetearyl sulfate, among the various ingredients. The emulsions were qualified for having good stability, based on the following stability tests:

i) heating the emulsion sample to 60° C., followed by centrifuging the sample at 3,000 rpm for 30 minutes ii) freezing the sample overnight at −15° C., followed by thawing the sample at room temperature iii) storing the sample at 45° C. for 90 days

TABLE II

| Ingredient | Phase | % by Weight 1 | 2 |
|---|---|---|---|
| Deionized Water | A | 43.484 | 38.650 |
| Glycerin | | 1.000 | 1.000 |
| Xanthan Gum (2% Solution) | | 5.000 | 10.000 |
| Preservative (Phenonip from Clariant) | | 0.800 | 1.000 |
| 50% Sodium Hydroxide | | 0.085 | 0.050 |
| Sodium Cetearyl Sulfate | | | 0.500 |
| Octylmethoxy Cinnamate | B | 7.500 | 7.500 |
| Octyl Salicylate | | 5.000 | 5.000 |
| Oxybenzone | | 6.000 | 6.000 |
| Isopropyl Myristate | | 2.500 | 3.000 |
| Sodium Cetearyl Sulfate | | | 1.000 |
| Cetearyl Glucoside (Tegocare CG 90 from Degussa) | | | 0.300 |
| Cetearyl Alcohol | | 2.500 | |
| Stearyl Alcohol | | | 3.000 |
| Glyceryl Stearate | | 3.000 | 3.000 |
| Polyethylene (AC 1702 from Honeywell) | | 3.000 | 3.000 |
| Tocopheryl Acetate | | 0.100 | |
| Astaxanthin (Antioxidant) | | 0.006 | |
| Deionized water | C | 2.000 | |
| Allantoin | | 0.100 | |
| Ascorbic acid | | 0.010 | |
| Dispersion 1 (Table I) | D | 17.500 (2% ZnO) | 17.500 (2% ZnO) |

Manufacturing Procedure

In a suitable vessel, combine the Phase A (water phase) ingredients.

Start heating the water phase to 90° C., while homogenizing it in a rotor-stator homogenizer (Silverson homogenizer).

Separately, combine all Phase B (oil phase) ingredients excepting polyethylene, and start heating the oil phase to 90° C. under gentle agitation.

Once the temperature of the oil phase reaches about 80° C., add polyethylene to the oil phase. Continue heating the oil phase to 90° C.

Once the polyethylene melts completely and is thoroughly mixed with the oil phase, add the heated oil phase to the heated water phase.

Homogenize the batch in Silverson for at least 10-15 minutes.

Start cooling the batch while it remains under propeller blade agitation.

Once the temperature reaches about 45° C., add the Phase C (Post-Add) ingredients to the batch. Mix well.

Add Phase D while continuing to mix the batch. Mix well until the batch looks homogeneous.

SPF Data

The emulsions 1 and 2 (Table II) were subjected to very water resistant, in-vivo SPF testing (conducted at Cantor Research Laboratories, Inc., New York) involving three panelists, as per the U.S. Federal Drug Administration protocol. The results of these tests are shown in Table III, demonstrating good water resistance property for both the sunscreen emulsions. Also, those familiar with the art will recognize that the given combination of sunscreens, as was used in these emulsions, ordinarily would not result in an SPF value of 52 in oil-in-water emulsion-based sunscreen compositions. Table IV shows the SPF values of several oil-in-water emulsion-based commercial sunscreen products, corresponding to various combinations of sunscreen actives. As apparent from Items No. 2 and 3 in Table IV, considerably higher levels of sunscreen actives (UV-absorbers) were required in the commercial formulations of Table IV than were required for the sunscreen compositions claimed herein (7.5% Octylmethoxy Cinnamate, 5% Octyl Salicylate, and 6% Oxybensozne, Table II) to achieve comparable SPF values.

TABLE III

| Emulsion (Table II) | Static SPF | Very Water Resistant SPF |
|---|---|---|
| 1 | 52.33 | 51.17 |
| 2 | 52.33 | 48.83 |

TABLE IV

| Item No. | Commercial Sunscreen Product | Sunscreen Combination | Label SPF | Comments |
|---|---|---|---|---|
| 1 | Du Pont Sunscreen Wipe, SPF 30 | 7.5% Octylmethoxy Cinnamate, 5% Octyl Salicylate, 5% Oxybenzone | 30 | |
| 2 | Neutrogena, Healthy Defense, Oil-Free, SPF 45 | 12% Homosalate, 7.5% Octylmethoxy Cinnamate, 5% Octyl Salicylate, 6% Oxybenzone, 2% Avobenzone | 45 | Avobenzone is a broad-spectrum (covering both UVA and UVB ranges of wavelength) sunscreen having a strong UVA absorption |
| 3 | Banana Boat Sport, SPF 50 | 10% Octocrylene, 7.5% Octylmethoxy Cinnamate, 5% Octyl Salicylate, 6% Oxybenzone | 50 | |

EXAMPLE III

This example shows the compositions of stable sunscreen emulsions of the present invention, wherein smectite clay, xanthan gum, and cross-linked polyacrylate (Carbopol 980) are used as the water-phase thickening agents. The emulsifiers used include an anionic emulsifier, sodium cetearyl sulfate. While containing 2% by weight of ZnO, these sunscreen emulsions did not show any apparent signs of separation of the oil phase nor of the water phase when subjected to the following stability tests:

i) heating the emulsion sample to 60° C., followed by centrifuging the sample at 3,000 rpm for 30 minutes ii) storing the sample at 45° C. for 90 days

TABLE V

| Ingredient | Phase | % by Weight 1 | 2 |
|---|---|---|---|
| Deionized Water | A | 23.600 | 23.660 |
| Glycerin | | 1.000 | 1.000 |
| Xanthan Gum (2% Solution) | | 5.000 | 5.000 |
| Preservative (Phenonip from Clariant) | | 0.800 | 0.800 |
| 50% Sodium Hydroxide | | 0.300 | 0.240 |
| Carbopol 980 (1% Solution) | | 10.000 | 7.000 |
| Octylmethoxy Cinnamate | B | 7.500 | 7.500 |
| Octyl Salicylate | | 5.000 | 5.000 |
| Oxybenzone | | 6.000 | 6.000 |
| Isopropyl Myristate | | 4.000 | 4.000 |
| Sodium Cetearyl Sulfate | | 1.000 | 1.000 |
| Cetearyl Glucoside (Tego care CG 90 from Degussa) | | 0.300 | 0.300 |
| Cetearyl Alcohol | | 1.000 | 1.000 |
| Methyl Glucose Sesquistearate (Tego Care PS from Degussa) | | 3.000 | 1.000 |
| Glyceryl Stearate | | 1.000 | 2.000 |
| Polyethylene (AC 1702 from Honeywell) | | 3.000 | 4.000 |
| Carbopol 980 (1% Solution) | C | 10.000 | 13.000 |
| Dispersion # 1 (Table I) | D | 17.500 | 17.500 |

EXAMPLE IV

This example shows the composition of a stable sunscreen emulsion of the present invention, which contains 5% by weight of ZnO. This sunscreen emulsion did not show any apparent signs of separation of the oil phase nor of the water phase when subjected to the following stability tests:

iii) heating the emulsion sample to 60° C., followed by centrifuging the sample at 3,000 rpm for 30 minutes iv) storing the sample at 50° C. for 30 days

TABLE VI

| Ingredients | Phase | % by Weight |
|---|---|---|
| Deionized Water | A | 47.900 |
| Glycerin | | 1.000 |
| Xanthan Gum | | 0.200 |
| Preservative (Phenonip from Clariant) | | 1.000 |
| 50% Sodium Hydroxide | | 0.100 |
| Octylmethoxy Cinnamate | B | 7.500 |
| Octyl Salicylate | | 5.000 |
| Oxybenzone | | 6.000 |
| Isopropyl Myristate | | 3.000 |
| Sodium Cetearyl Sulfate | | 1.000 |
| Cetearyl Glucoside (Tego care CG 90 from Degussa) | | 0.300 |
| Cetearyl Alcohol | | 3.000 |
| Glyceryl Stearate | | 3.000 |
| Dispersion # 2 (Table I) | C | 21.000 |

The invention claimed is:

1. A method of protecting a surface from UV radiation comprising coating the surface with a stable, oil-in-water (O-W) emulsion-based sunscreen composition having at least one water-insoluble, organic UV-absorber having a water-solubility of less than 0.1% by weight, contained in the oil phase of the sunscreen emulsion, comprising i) zinc oxide (ZnO) particles having a surface free of any prior coating of any inorganic oxide and hydrophobic material, remaining dispersed in the water phase of the sunscreen emulsion; ii) at least one non- or low-foaming, non-cationic, water-soluble hydrophilic polymer having a weight average molecular weight in the range of 1,000 to 50,000 Dalton, capable of dispersing or deflocculating the ZnO particles but incapable of thickening an aqueous composition to a viscosity of greater than 100 cps at 25° C., wherein the viscosity is measured using a Brookfield viscometer operated at 10 rpm for 15 seconds, when the polymer is added at an amount of 1%, based on the total weight of the hydrophilic polymer and water in the aqueous composition; iii) at least one phenolic polymer, capable of functioning as a dispersing or deflocculating agent for particulate material(s), and adsorbing at an oil-water interface; and iv) a buffering agent for the water phase of the sunscreen emulsion.

2. The method of claim 1 wherein the ZnO particles comprise from 2 to 25% by weight of the composition, and have a mean particle size of less than 2 micrometers (microns).

3. The method of claim 1 wherein the non- or low-foaming hydrophilic polymer is sodium polyacrylate comprising from 0.01 to 10% by weight of the composition.

4. The method of claim 1 wherein the phenolic polymer is selected from the group consisting of lignosulfonate, lignin, oxylignin, humate, and mixtures thereof.

5. The method of claim 4 wherein the phenolic polymer comprises from 0.0005 to 1% by weight of the composition.

6. The method of claim 1 wherein the oil phase comprises from 1 to 60% by weight of the composition.

7. The method of claim 1 wherein the organic UV absorber is selected from the group consisting of octyl methoxycinamate, homosalate, octocrylene, octyl salicylate, methylbenzylidene camphor, phenylbenzylimaid-azole sulfonic acids, ethylhexyl triazone, oxybenzone, methyl anthranilate, avobenzone, and mixtures thereof.

8. The method of claim 1 wherein the buffering agent is borax, comprising from 0.1 to 5% by weight of the composition.

9. The method of claim 1 further containing one or more particulate material other than ZnO, remaining dispersed in the water phase of the sunscreen emulsion.

10. The method of claim 9 wherein the non-ZnO particulate material is selected from the group consisting of inorganic oxide, silicate minerals, water-insoluble inorganic salts, and organic latex polymers, having a mean particle size of less than 5 microns.

11. The method of claim 10 wherein the non-ZnO particulate material is included in the composition in an amount from 0.05 to 3% by weight of the composition.

12. The method of claim 1, wherein the surface being protected is human skin.

13. A method of protecting a surface from UV radiation comprising coating the surface with a composition comprising i) water; ii) zinc oxide (ZnO) particles having a surface free of any prior coating of any inorganic oxide and any hydrophobic material, remaining dispersed in the water phase of the sunscreen emulsion; iii) one or more non- or low-foaming, water-soluble hydrophilic polymer, capable of functioning as a dispersing or deflocculating agent for the ZnO particles but incapable of thickening an aqueous composition to a viscosity of greater than 100 cps at 25° C., wherein the viscosity is measured using a Brookfield viscometer operated at 10 rpm for 15 seconds, when the hydrophilic polymer is added at an amount of 1%, based on the total weight of the polymer and water in the aqueous composition; iv) one or more phenolic polymer, capable of dispersing or deflocculating particulate material(s), and adsorbing at an oil-water interface; and v) a buffering agent.

14. The method of claim 13 wherein the ZnO particles comprise from 2 to 60% by weight of the composition, and have a mean particle size of less than 2 micrometer (micron).

15. The method of claim 13 wherein the non- or low-foaming hydrophilic polymer is sodium polyacrylate having a molecular weight in the range of 1,000-50,000 Dalton, comprising from 0.02 to 30% by weight of the compositions.

16. The method of claim 13 wherein the phenolic polymer is selected from the group consisting of lignosulfonate, lignin, oxylignin, humate, and mixtures thereof.

17. The method of claim 16 wherein the phenolic polymer comprises from 0.01 to 30% by weight of the composition.

18. The method of claim 13 wherein the buffering agent is borax, comprising from 0.5 to 10% by weight of the composition.

19. The method of claim 13 further containing one or more particulate material other than ZnO.

20. The method of claim 13 wherein the non-ZnO particulate material is selected from the group consisting of inorganic oxide, silicate minerals, water-insoluble inorganic salts, and organic latex polymers, having a mean particle size of less than 5 microns.

21. The method of claim 20 wherein the non-ZnO particulate material is included in the composition in an amount from 0.1 to 30% by weight of the composition.

22. The method of claim 13, wherein the composition is included in a water phase of a water-in-oil emulsion-based sunscreen composition.

23. The method of claim 15, wherein the composition is included in a water phase of an oil-in-water emulsion-based sunscreen composition.

24. The method of claim 17, wherein the composition is included in a water-based sunscreen composition.

25. The method of claim 13 comprising coating the surface with the composition of claim 23.

* * * * *